United States Patent
Gatti et al.

(10) Patent No.: US 6,596,697 B2
(45) Date of Patent: *Jul. 22, 2003

(54) INJECTABLE READY-TO-USE SOLUTIONS CONTAINING AN ANTITUMOR ANTHRACYCLINE GLYCOSIDE

(75) Inventors: Gaetano Gatti, Sesto San Giovanni (IT); Diego Oldani, Robecco sul Naviglio (IT); Giuseppe Bottoni, Bergamo (IT); Carlo Confalonieri, Cusano Milanino (IT); Luciano Gambini, Cornaredo (IT); Roberto De Ponti, Milan (IT)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/945,539

(22) Filed: Aug. 30, 2001

(65) Prior Publication Data

US 2002/0077303 A1 Jun. 20, 2002

Related U.S. Application Data

(63) Continuation of application No. 09/149,360, filed on Sep. 8, 1998, now Pat. No. 6,284,738, which is a continuation of application No. 07/827,742, filed on Jan. 29, 1992, now Pat. No. 6,107,285, which is a division of application No. 07/503,856, filed on Apr. 3, 1990, now Pat. No. 5,124,317, which is a division of application No. 07/385,999, filed on Jul. 27, 1989, now Pat. No. 4,946,831, which is a continuation of application No. 06/878,784, filed on Jun. 26, 1986, now abandoned.

(30) Foreign Application Priority Data

Aug. 2, 1985 (GB) .............................. 8519452

(51) Int. Cl.$^7$ .............................................. A61K 31/70
(52) U.S. Cl. .......................................... 514/34; 536/6.4
(58) Field of Search .............................. 514/34; 536/6.4

(56) References Cited

U.S. PATENT DOCUMENTS

| | | | |
|---|---|---|---|
| 4,109,076 A | 8/1978 | Henry et al. |
| 4,296,105 A | 10/1981 | Baurain et al. |
| 4,537,593 A | 8/1985 | Alchas |
| 4,564,054 A | 1/1986 | Gustavsson |
| 4,576,211 A | 3/1986 | Valentini et al. |
| 4,588,403 A | 5/1986 | Weiss et al. |
| 4,786,281 A | 11/1988 | Valentini et al. |

FOREIGN PATENT DOCUMENTS

| | | |
|---|---|---|
| CA | 1005760 | 2/1977 |
| CA | 1129344 | 8/1982 |
| CA | 1203482 | 4/1986 |
| EP | 401896 A1 | 12/1990 |
| FR | 2405957 | 5/1979 |
| GB | 2178311 | 2/1987 |

OTHER PUBLICATIONS

Beijnen et al. (1985), "Stability of Anthracycline Antitumor Agents in Infusion Fluids," J. Parenteral Science and Technology, vol. 39, pp. 220–222.

The Merck Index (1983), "Doxorubicin," 10$^{th}$ Edition, AN–3435, p. 499.

Kano et al., Electrochemical Properties of Adriamycin Adsorbed on a Mercury Electrode Surface, The Chemical Society of Japan. Bull. Chem. Soc. Jpn., 57, 2383–2390 (1984).

Kano et al., The Effects of the pH and the Temperature on the Oxidation–reduction Properties of Adriamycin Adsorbed on a Mercury Electrode Surface, The Chemical Society of Japan, Bull. Chem. Soc. Jpn., 58, 424–428 (1985).

Arcamone et al. (1969, "Adriamycin, 14–Hydroxydaunomycin, a New Antitumor Antibiotic from *S. Prucetius* Var. Caesius," *Biotechnology and Bioengineering*, vol. XI, pp. 1101–1110.

Despois et al. (1967), "Isolement D'un Nouvel antibiotique Doue D'Activite Antitumorale: La Rubidomycine (13.057 R.P.) Identite De La Rubidomycine et de La Daunomycine," Path. Biol., vol. 15, pp. 887–891.

Lokich et al. (1983), "Constant Infusion Schedule for Adrimycin: A Phase I–II Clinical Trial of A 30–Day Schedule by Ambulatory Pump Delivery System," *J. Clinical Oncology*, vol. 1, pp. 24–28.

Wasserman and Bundgaard (1983), "Kinetics of the Acid–Catalyzed Hydrolysis of Doxorubicin," *International J. Pharmaceutics*, vol. 14, pp. 73–78.

Merck Index (1996), Mitoxantrone, 12$^{th}$ Edition, Entry 6303, p. 1064.

Martindale (1989), Mitotone, *The Pharmaceutical Press*, 29$^{th}$ Edition, London, Entry 1852–x, pp. 643–645.

ABPI Data Sheet Compendium, 1994–1995, "Novantron Injection," Lederle Laboratories, pp. 752–754.

Geigy Scientific Tables, vol. 3, *Physical Chemistry Composition of Blood Hematology Somatometric Data*, 8$^{th}$ revised and enlarged edition, Edited by C. Lentner, pp. 54–60.

Dorr (1979), "Incompatibilities with Parenteral Anticancer Drugs," *The American Journal of Intravenous Therapy*, Feb./Mar., pp. 42, 45–46, 52.

(List continued on next page.)

*Primary Examiner*—Elli Peselev
(74) *Attorney, Agent, or Firm*—McDonnell Boehnen Hulbert & Berghoff

(57) ABSTRACT

According to the invention there is provided a sterile, pyrogen-free, ready-to-use solution of an anthracycline glycoside, especially doxorubicin, which consists essentially of a physiologically acceptable salt of an anthracycline glycoside dissolved in a physiologically acceptable solvent therefor, which has not been reconstituted from a lyophilizate and which has a pH of from 2.5 to 6.5. The solution of the invention is particularly advantageous for the administration by injection of the anthracycline glycoside drugs, e.g. doxorubicin, in the treatment of both human and animal tumors.

30 Claims, No Drawings

OTHER PUBLICATIONS

Bernard, J., et al. (1969) *Rubidomycin*, Springer–Verlag, Berlin–Heidelberg–New York.

Karlsen, J., et al (1983), "Stability of Cytotoxic Intravenous Solutions Subjected to Freeze–Thaw Treatment," *Nor. Pharm ACTA*, vol. 45, pp. 61–67.

Vogelzang, N.J., et al. (1985), "Phase I Trial of an Implanted Battery–Powered Programmable Drug Delivery System for Continuous Doxorubicin Administration," *Journal of Clinical Oncology*, vol. 3, No. 3 (Mar.), pp. 407–414.

Europaischez Arneibuch, vol. III, 1979, p. 654 (English translation provided).

Arcamone et al. (1972), "Structure and Physiochemical Properties of Adriamycin (Doxorubicin)," International Symposium on Adriamycin, Springer–Verlag, Berlin, pp. 9–22.

Beijnen, J.H. et al. (1985), "Aspects of the Chemical Stability of Doxorubicin and Seven Other Anthracyclines in Acidic Solution," *Pharmaceutisch Weekblad Scientific Edition*, vol. 7, pp. 109–116.

German Patent Office Decision dated Oct. 8, 1996 (English translation attached) revoking Patent No. 3621844.

Wang and Kowal (1980), "Review of Excipients and pH's for Parenteral Products Used in the United States," *J. of the Parenteral Drug Association*, vol. 14, p. 452–462.

Harris, Daniel C. (1995), "Quantitative Chemical Analysis," 4th Edition, W.H. Freeman and Company.

Tan, C. et al. Daunomycin, an Anti–Tumor Antibiotic, in the Treatment of Neoplastic Disease, Mar. 1967, *Cancer* 20:333–353.

Samuels, L.D., et al, "Daunorubicin Therapy in Advanced Neuroblastoma", Apr. 1971, *Cancer* 27:831–834.

Miller, A.A. and Schmidt, C.G., "Clinical Pharmacology and Toxocology of 4" –O–Tetrahydropyranyladriamycin, Mar. 1, 1987, *Cancer Research* 47:1461–1465.

Holton, C.P. et al. "Clinical Study of Daunomycin and Prednisone for Induction of Remission in Children with Advanced Lukemia", *New England Journal of Medicine*, Jan. 23, 1969, 280:171–174.

Rozencweig, M. et al., "Preliminary Experience with Marcellomycin: Pre–Clinical and Clinical Aspects" p. 549–561.

Bradner and Misiek, (1977) *The Journal of Antibiotics*, "Bohemica Acid Complex. Biological Characterization of the Antibiotics, Musettamycin and Marcellomycin," 30(6) 519–522.

Kjeld Ilver, Almen Galenisk Farmaci—Foreloesningsnoter, Dansk Farmaceutforenings Forlag 1971, pp. 132–136. (English translation provided).

Gjelstrup et al. (1983), Almen Farmaaci I, Dansk Farmaceutforenings Forlag, København, pp. 404–408, 440, 442–443, 447, 451. (English translation provided).

Erik Sandell, (1967), *Galenisk Farmaci*, 2nd edition, Stockholm, pp. 214. (English translation provided).

Erik Sandell, (1982), *Galenisk Farmaci*, 3rd edition, Stockholm, pp. 123. (English translation provided).

Svend Aage Schou & V. Gaunø Jensen (1959), *Træk of en flaeniske farmaci*, Store Nordiske Videnskabsboghandel, pp. 220 (English translation provided).

Arcamone, F. (1977), *Lloydia*, "New Antitumor Anthracyclines," 40(1):45–66.

Naff et al., (1982) *Anthracycline Antibiotics*, Anthracyclines in the National Cancer Institute Program, Hassan S. El Khadham, editor, Academic Press, pp. 1–57.

*Formularium Der Nederlandse Apothekers*, (1983), pp. I.8, I.24, I.63.

*Formularium Der Nederlandse Apothekers*, (1979), pp. I.64, I.82.

*Formularium Der Nederlandse Apothekers*, (1985), pp. I.64a.

*Formularium Der Nederlandse Apothekers*, (1989), pp. I.88.

*Formularium Der Nederlandse Apothekers*, (1992), pp. I.63.a.

Bohme and Harke (1979), *Europäisches Arzneibuch, Band III*, Kommentar, Wissenschaftliche Verlagsgesellschaft mbH Stuttgart, pp. 654 (English Translation provided).

Arcamone et al. (1972). "Structure and Physiochemical Properties of Adriamycin (Doxorubicin)," *International Symposium on Adriamycin*, pp. 9–22.

Wang and Kowal (1980), "Review of Excipients and pH's for Parenteral Products Used in the United States," *Journal of the Parenteral Drug Association*, pp. 452–462.

Harris, *Quantitative Chemical Analysis*, Fourth Edition, W.H. Freeman & Company, New York, pp. 240.

Bernard et al., editors (1969), *Rubidomycin A New Agent Against Cancer*, pp. ix–181.

Karlsen et al. (1983), "Stability of cytotixic intravenous solutions subjected to freeze–thaw treatment," *Nor. Pharm. Acta*. 45, 61–67.

*Topics in Antibiotic Chemistry*, 2, 109–115, 1978.

*The Interpharm International Dictionary of Biotechnology and Pharmaceutical Manufacturing*, edited By Dean E. Snyder, Publisher Buffalo Grove, IL: Interpharm Press, Inc., 1992.

Merck Index, 10th edition, 1983, p. 499, Entry No. 3435.

Bosanquet, "Stability of solutions of antineoplastic agents during preparation and storage for in vitro assays", *Cancer Chemotherapy and Pharmacology*, vol. 17, 1986, pp. 1–10.

Rolf Kaltofen, Joachim Ziemann et al., Tabellenbuch Chemie, 12th edition, pp. 172, 181.

Yüksel, "Determination of Ceftriaxone in Aqueous Humour and Serum Samples by Differential–pulse Adsorptive Stripping Voltammetry", *Analyst*, vol. 119, 1994, pp. 1575–1577.

Falbe et al., *Rompp. Chemie Lexikon*, 9th edition, Georg Thieme Verlag Stuttgart, New York, 1992, "Buffers", pp. 3677–3678.

Mortimer, *Chemie*, 3rd edition, Georg Thieme Verlag Stuttgart, New York, 1980, pp. 490–494.

Falck, K., et al. (1979), "Mutagenicity in Urine of Nurses Handling Cytostatic Drugs", *The Lancet*, Jun. 9, 1979, p. 1250–1251.

"Union Warns of Cancer Drug Dangers", *Chemistry and Industry*, Jul. 4, 1983.

Lassila, O., et al. (1980), "Immune Function in Nurses Handling cytostatic Drugs", *The Lancet*, Aug. 30, 1980., p. 482.

Abstract of Medical Economics Co., Chemistry–Industry, Feb. 7, 1983, p. 99.

*Chemical Abstract*, vol. 99, p. 345 (1983), Abst. No. 99:218014y.

INJECTABLE READY-TO-USE SOLUTIONS CONTAINING AN ANTITUMOR ANTHRACYCLINE GLYCOSIDE

This is a continuation application of U.S. application Ser. No. 09/149,360, filed Sep. 8, 1998 now U.S. Pat. No. 6,284,738, which is a continuation application of U.S. application Ser. No. 07/827,742, filed Jan. 29, 1992 now U.S. Pat. No. 6,107,285, which is a divisional application of U.S. Ser. No. 07/503,856, filed Apr. 3, 1990 now U.S. Pat. No. 5,124,317, which is a divisional application of U.S. Ser. No. 07/385,999, filed Jul. 27, 1989 now U.S. Pat. No. 4,946,831, which in turn is a continuation application of U.S. Ser. No. 06/878,784, filed Jun. 26, 1986, now abandoned.

The present invention relates to a stable intravenously injectable ready-to-use solution of an antitumor anthracycline glycoside, e.g. doxorubicin, to a process for preparing such a solution, and provide the same in a sealed container, and to a method for treating tumors by the use of the said ready-to-use solution.

The anthracycline glycoside compounds are a well known class of compounds in the antineoplastic group of agents, wherein doxorubicin is a typical, and the most widely used, representative: Doxorubicin. Anticancer Antibiotics, Federico Arcamone, 1981, Publ: Academic Press, New York, N.Y.; Adriamycin Review, EROTC International Symposium, Brussels, May, 1974, edited by M. Staquet. Publ. Eur. Press Medikon, Ghent, Belg.; Results of Adriamycin Therapy, Adriamycin Symposium at Frankfurt/Main 1974 edited by M. Ghione, J. Fetzer and H. Maier, publ.: Springer, New York, N.Y.

At present, anthracycline glycoside antitumor drugs, in particular, e.g., doxorubicin, are solely available in the form of lyophilized preparations, which need to be reconstituted before administration. Both the manufacturing and the reconstitution of such preparations expose the involved personnel (workers, pharmacists, medical personnel, nurses) to risks of contamination which are particularly serious due to the toxicity of the antitumor substances. The Martindale Extra Pharmacopoeia 28th edition, page 175 left column, reports, indeed, about adverse effects of antineoplastic drugs and recommends that "They must be handled with great care and contact with skin and eyes avoided; they should not be inhaled. Care must be taken to avoid extravasation since pain and tissue damage may ensue."

Similarly, Scand. J. Work Environ Health vol. 10 (2), pages 71–74 (1984), as well as articles on Chemistry Industry, Issue Jul. 4, 1983, page 488, and Drug-Topics-Medical-Economics-Co, Issue Feb. 7, 1983, page 99 report about severe adverse effects observed in medical personnel exposed to use of cytostatic agents, including doxorubicin.

To administer a lyophilized preparation, double handling of the drug is required, the lyophilized cake having to be first reconstituted and then administered and, moreover, in some cases, the complete dissolution of the powder may require prolonged shaking because of solubilization problems.

As the risks connected with the manufacturing and the reconstitution of a lyophilized preparate would be highly reduced if a ready-to-use solution of the drug were available, we have developed a stable, therapeutically acceptable intravenously injectable solution of an anthracycline glycoside drug, e.g. doxorubicin, whose preparation and administration does not require either lyophilization or reconstitution.

According to the present invention, there is provided a sterile, pyrogen-free, anthracycline glycoside solution which consists essentially of a physiologically acceptable salt of an anthracycline glycoside dissolved in a physiologically acceptable solvent therefor, which has not been reconstituted from a lyophilizate and which has a pH of from 2.5 to 6.5.

Preferably the solution of the invention is provided in a sealed container.

Preferably the anthracycline glycoside is chosen from the group consisting of doxorubicin, 4'-epi-doxorubicin (i.e. epirubicin), 4'-desoxy-doxorubicin (i.e. esorubicin), 4'-desoxy-4'-iodo-doxorubicin, daunorubicin and 4-demethoxydaunorubicin (i.e. idarubicin).

A particularly preferred anthracycline glycoside is doxorubicin.

Any physiologically acceptable salt of the anthracycline glycoside may be used for preparing the solution of the invention. Examples of suitable salts may be, for instance, the salts with mineral inorganic acids such as hydrochloric, hydrobromic, sulfuric, phosphoric, nitric and the like, and the salts with certain organic acids such as acetic, succinic, tartaric, ascorbic, citric, glutammic, benzoic, methanesulfonic, ethanesulfonic and the like. The salt with hydrochloric acid is a particularly preferred salt, especially when the anthracycline glycoside is doxorubicin.

Any solvent which is physiologically acceptable and which is able to dissolve the anthracycline glycoside salt may be used. The solution of the invention may also contain one or more additional components such as a co-solubilizing agent (which may be the same as a solvent), a tonicity adjustment agent and a preservative. Examples of solvents, co-solubilizing agents, tonicity adjustment agents and preservatives which can be used for the preparation of the anthracycline glycoside solutions of the invention are hereunder reported.

Suitable solvents and co-solubilizing agents may be, for instance, water; physiological saline; aliphatic amides, e.g. N,N-dimethylacetamide, N-hydroxy-2-ethyl-lactamide and the like; alcohols, e.g. ethanol, benzyl alcohol and the like; glycols and polyalcohols, e.g. propyleneglycol, glycerin and the like; esters of polyalcohols, e.g. diacetine, triacetine and the like; polyglycols and polyethers, e.g. polyethyleneglycol 400, propyleneglycol methylethers and the like; dioxolanes, e.g. isopropylidenglycerin and the like; dimethylisosorbide; pyrrolidone derivatives, e.g. 2-pyrrolidone, N-methyl-2-pyrrolidone, polyvinylpyrrolidone (co-solubilizing agent only) and the like; polyoxyethylenated fatty alcohols, e.g. Brij® and the like; esters of polyoxyethylenated fatty acids, e.g. Cremophor®, Myij® and the like; polysorbates, e.g. Tweens®; polyoxyethylene derivatives of polypropyleneglycols, e.g. Pluronics®.

A particularly preferred co-solubilizing agent is polyvinylpyrrolidone.

Suitable tonicity adjustment agents may be, for instance, physiologically acceptable inorganic chlorides, e.g. sodium chloride, dextrose, lactose, mannitol and the like.

Preservatives suitable for physiological administration may be, for instance, esters of para-hydroxybenzoic acid (e.g., methyl, ethyl, propyl and butyl esters, or mixtures of them), chlorocresol and the like.

The above mentioned solvents and co-solubilizing agents, tonicity adjustment agents and preservatives can be used alone or as a mixture of two or more of them.

Examples of preferred solvents are water, ethanol, polyethyleneglycol and dimethylacetamide as well as mixtures in various proportions of these solvents. Water is a particularly preferred solvent.

To adjust the pH within the range of from 2.5 to about 5.0 a physiologically acceptable acid may be added as desired. The acid may be any physiologically acceptable acid, e.g., an inorganic mineral acid such as hydrochloric, hydrobromic, sulfuric, phosphoric, nitric and the like, or an organic acid such as acetic, succinic, tartaric, ascorbic, citric, glutammic, benzoic, methanesulphonic, ethanesulfonic and the like, or also an acidic physiologically acceptable buffer solution, e.g., a chloride buffer, an acetate buffer, a phosphate buffer and the like.

For obtaining pH values from about 5 to about 5.5 the addition of the acid is not, usually, necessary, but only addition of a physiologically acceptable buffer solution, e.g., one of those indicated above, may be required, as desired.

For obtaining pH values from about 5.5 to 6.5 the addition of a physiologically acceptable alkalinizing agent, such as sodium hydroxide, a mono, di- or triethanolamine or the like, or, preferably, a buffer solution such as a phosphate buffer, a TRIS buffer or the like is required.

The preferred range of pH for the ready-to-use solution of the invention is from 2.5 to 5.5, in particular from about 3 to about 5.2, a pH of about 3 and a pH of about 5 being particularly preferred values.

In the solutions of the invention the concentration of the anthracycline glycoside may vary within broad ranges, preferably from 0.1 mg/ml to 100 mg/ml, in particular from 0.1 mg/ml to 50 mg/ml, most preferably from 1 mg/ml to 20 mg/ml.

The preferred ranges of concentration may be slightly different for different anthracycline glycosides. Thus, for example, preferred concentrations for doxorubicin are from about 2 mg/ml to about 50 mg/ml, preferably from 2 mg/ml to 20 mg/ml, particularly appropriate values being 2 mg/ml and 5 mg/ml. Similar concentrations are preferred also for 4'-epi-doxorubicin, 4'-desoxy-doxorubicin and 4'-desoxy-4'-iodo-doxorubicin. Preferred ranges of concentration for daunorubicin and 4-demethoxy-daunorubicin are from 0.1 mg/ml to 50 mg/ml, preferably from 1 mg/ml to 20 mg/ml, concentrations of 1 mg/ml and 5 mg/ml being particularly appropriate.

Suitable packaging for the anthracycline glycoside solutions may be all approved containers intended for parenteral use, such as plastic and glass containers, ready-to-use syringes and the like. Preferably the container is a sealed glass container, e.g. a vial or an ampoule.

According to a particularly preferred feature of the invention, there is provided a sterile, pyrogen-free, doxorubicin solution which consists essentially of a physiologically acceptable salt of doxorubicin dissolved in a physiologically acceptable solvent therefor, which has not been reconstituted from a lyophilizate and which has a pH of from 2.5 to 6.5.

In the above indicated preferred feature of the invention the physiologically acceptable salt of doxorubicin may be, e.g. the salt with a mineral inorganic acid such as hydrochloric, hydrobromic, sulfuric, phosphoric, nitric and the like, or the salt with an organic acid such as acetic, succinic, tartaric, ascorbic, citric, glutammic, benzoic, methanesulfonic, ethanesulfonic and the like. The hydrochloride salt is a particularly preferred salt.

For the solution hereabove indicated as a preferred feature of the invention suitable solvents, co-solubilizing agents, tonicity adjustment agents and preservatives may be the same as those previously recited in the specification. Water is a particularly preferred solvent.

Also, the physiologically acceptable acid which may be added to adjust the pH to from 2.5 to about 5, if desired, and the alkanilizing agent which may be added to adjust the pH, if desired, to a value from about 5.5 to 6.5 may be one of those previously specified. When it is desired to adjust the pH of the above said preferred solution to a value of from 2.5 to about 5, hydrochloric acid is an especially preferred acid. Preferred pH values for the above said preferred solutions of the invention are from 2.5 to 5.5, in particular from about 3 to about 5.2, the pH values of 3 and 5 being especially preferred.

Though the concentration of doxorubicin in the above preferred feature may vary within the broad range from 0.1 mg/ml to 100 mg/ml, preferred concentrations are from 2 mg/ml to 50 mg/ml, most preferably from 2 mg/ml to 20 mg/ml: examples of especially preferred concentrations of doxorubicin are 2 mg/ml and 5 mg/ml.

The invention also provides a process for producing a sterile, pyrogen-free anthracycline glycoside solution with a pH of from 2.5 to 6.5, which process comprises dissolving a physiologically acceptable salt of the anthracycline glycoside, which salt is not in the form of a lyophilizate, in a physiologically acceptable solvent therefor; optionally adding a physiologically acceptable acid or buffer to adjust the pH within the said range as desired; and passing the resulting solution through a sterilising filter.

One or more additional components such as co-solubilizing agents, tonicity adjustment agents and preservatives, for instance of the kind previously specified, may be added to the solution prior to passing the solution through the sterilising filter.

With the solutions of the invention it is possible to obtain compositions having a very high concentration of the anthracycline glycoside active substance even at 50 mg/ml and more. This constitutes a great advantage over the presently available lyophilized preparates wherein high concentrations of anthracycline glycoside can only be obtained with difficulty because of solubilization problems encountered in reconstitution, mainly with saline. The presence of the excipient, e.g. lactose, in the lyophilized cake, and its generally high proportion in respect of the active substance, even up to 5 parts of excipient per part of active substance, has a negative effect on solubilization so that difficulties may arise in obtaining dissolution of the lyophilized cake, especially for concentrations of anthracycline glycoside higher than 2 mg/ml.

The solutions of the invention are characterized by a good stability. Solutions in various solvents and with different pH's and concentrations have been found to be stable for long periods at temperatures accepted for the storage of pharmaceutical preparations. This is illustrated in the Examples which follow.

Owing to the well known anti-tumor activity of the anthracycline glycoside active drug substance, the pharmaceutical compositions of the invention are useful for treating tumors in both human and animal hosts. Examples of tumors that can be treated are, for instance, sarcomas, including osteogenic and soft tissue sarcomas, carcinomas, e.g., breast-, lung-, bladder-, thyroid-, prostate- and ovarian carcinoma, lymphomas, including Hodgkin and non-Hodgkin lymphomas, neuroblastoma, melanoma, myeloma, Wilms tumor, and leukemias, including acute lymphoblastic leukemia and acute myeloblastic leukemia. Examples of specific tumours that can be treated are Moloney Sarcoma Virus, Sarcoma 180 Ascites, solid Sarcoma 180, gross transplantable leukemia, L 1210 leukemia and lymphocytic P 368 leukemia.

Thus, according to the invention there is also provided a method of inhibiting the growth of a tumour, in particular one of those indicated above, which comprises administering to a host suffering from said tumour an injectable solution according to the invention containing the active drug substance in an amount sufficient to inhibit the growth of said tumour.

The injectable solutions of the invention are administered by rapid intravenous injection or infusion according to a variety of possible dose schedules. Suitable dose schedule for doxorubicin may be, for example, of 60 to 75 mg of active drug substance per $m^2$ of body surface given as a single rapid infusion and repeated at 21 days; an alternative schedule may be of 30 mg/$m^2$ day by intravenous route for 3 days, every 25 days. Suitable dosages for 4'-epi-doxorubicin and 4'-desoxy-doxorubicin may be, for instance, of 75 to 90 mg/$m^2$ given in a single infusion to be repeated at 21 days, and similar dosages may be useful for 4'-desoxy-4'-iodo-doxorubicin.

Idarubicin, i.e. 4-demethoxy-daunorubicin, may be, e.g., administered intravenously at a single dose of 13–15 mg/$m^2$ every 21 days in the treatment of solid tumours, while in the treatment of leukemias a preferred dose schedule is, e.g., of 10–12 mg/$m^2$ day by intravenous route for 3 days, to be repeated every 15–21 days; similar dosages may be, e.g., followed also for daunorubicin.

The following examples illustrate but do not limit in any way the invention.

With reference to the examples, the stability controls on the ready-to-use solutions were carried out by means of high performance liquid chromatography (HPLC), at the following experimental conditions:

| | |
|---|---|
| Liquid chromatograph | : Varian model 5010 |
| Spectrophotometric detector | : Knauer model 8700 |
| Integrating recorder | : Varian model CDS 401 |
| Injection valve | : Rheodyne model 7125 fitted with a 10 mcl sample loop |
| Chromatographic column | : Waters $\mu$-Bondapak C18 (length = 300 mm; inner diameter = 3.9 mm; average particle size = 10 mcm) |
| Column temperature | : ambient (about 22° C. ± 2° C.) |
| Mobile phase | : water: acetonitrile (69:31 v/v) adjusted top pH 2 with phosphoric acid, filtered (sintered glass filter, 1 mcm or finer porosity) and deaerated |
| Mobile phase flow rate | : 1.5 ml/min |
| Analytical wavelength | : 254 ± 1 nm |
| Integrating recorder sensitivity | : 512 |
| Chart speed | : 1 cm/min |

At these conditions, the peak of the anthracycline glycoside showed a retention time of about 6 minutes.

The obtained results are reported in the Tables accompanying the examples.

The extrapolation of the analytical data in order to determine the time when the 90% of the initial assay could be expected ($t_{90}$ value) was made following an Arrhenius plot.

This procedure of analytical data treatment is well known and widely used and described in the art: see, e.g., Chemical Stability of Pharmaceuticals, Kennet A. Connors, Gordon L. Amidon, Lloyd Kennon, Publ. John Wiley and Sons, New York, N.Y., 1979.

The term "teflon" refers to "Teflon™".

EXAMPLE 1

| Composition | for 80 vials | (for 1 vial) |
|---|---|---|
| Doxorubicin · HCl | 0.8 g | (10 mg) |
| Water for injections q.s. to | 0.4 l | (5 ml) |

Doxorubicin.HCl (0.80 g) was dissolved in 90 percent of the amount of water for injections, de-aerated by nitrogen bubbling. The pH of the solution was not adjusted. Further de-aerated water for injections was then added to bring the solution to its final volume (0.40 l).

The solution was filtered through a 0.22 $\mu$m microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 12 weeks (4° C.).

The stability data obtained, using high performance liquid chromatography (HPLC) for the determination of potency, are reported in the following Table 1:

TABLE 1

INITIAL VALUES
Concentration: 1.994 mg/ml    pH = 5.2
Relative % Assay: 100.0

| | TEMPERATURE | | | | | | | |
|---|---|---|---|---|---|---|---|---|
| | 4° C. | | 35° C. | | 45° C. | | 55° C. | |
| TIME (weeks) | Conc. mg/ml | Rel. % Assay | Conc. mg/ml | Rel. % Assay | Conc. mg/ml | Rel. % Assay | Conc. mg/ml | Rel. % Assay |
| 1 | 1.992 | 99.9 | 1.917 | 96.1 | 1.768 | 88.7 | 1.493 | 75.0 |
| 2 | | | 1.843 | 92.4 | 1.618 | 81.1 | 1.166 | 58.5 |
| 3 | | | 1.774 | 89.0 | 1.506 | 75.5 | 0.830 | 41.6 |
| 4 | 1.974 | 99.0 | 1.720 | 86.3 | 1.393 | 69.9 | | |
| 12 | 1.980 | 99.3 | | | | | | |

$t_{90}$ (days) extrapolated according to Arrhenius equation:
$t_{90}$ at 4° C. = 815 days
$t_{90}$ at 8° C. = 480 days Similar stability data can be observed also for analogous solutions containing either doxorubicin hydrochloride at 5 mg/ml concentration, or 4'-epi-doxorubicin, 4'-desoxy-doxorubicin, 4'-desoxy-4'-iodo-doxorubicin, daunorubicin or 4-demethoxy-daunorubicin, as hydrochloride salts, at both 2 mg/ml and 5 mg/ml concentration.

EXAMPLE 2

| Composition | for 80 vials | (for 1 vial) |
|---|---|---|
| Doxorubicin · HCl | 0.8 g | (10 mg) |
| Hydrochloric acid 0.1N q.s. to | pH = 3 | (pH = 3) |
| Water for injections q.s. to | 0.4 l | (5 ml) |

Doxorubicin.HCl (0.8 g) was dissolved in 90 percent of the amount of water for injections, de-aerated by nitrogen bubbling. The hydrochloric acid was then added dropwise to adjust the pH of the solution to 3. Further de-aerated water for injections was then added to bring the solution to its final volume (0.4 l).

The solution was filtered through a 0.22 μm microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 12 weeks (4° C.).

The stability data obtained, using high performance liquid chromatography (HPLC) for the determination of potency, are reported in the following Table 2:

TABLE 2

INITIAL VALUES
Concentration: 1.992 mg/ml    pH = 3.0
Relative % Assay: 100.0

TEMPERATURE

| TIME (weeks) | 4° C. | | 35° C. | | 45° C. | | 55° C. | |
|---|---|---|---|---|---|---|---|---|
| | Conc. mg/ml | Rel. % Assay | Conc. mg/ml | Rel. % Assay | Conc. mg/ml | Rel. % Assay | Conc. mg/ml | Rel. % Assay |
| 1 | 1.995 | 100.2 | 1.952 | 98.0 | 1.919 | 96.3 | 1.493 | 75.0 |
| 2 | | | 1.889 | 94.8 | 1.851 | 92.9 | 1.036 | 51.9 |
| 3 | | | 1.876 | 94.2 | 1.565 | 78.6 | 0.730 | 36.7 |
| 4 | 1.979 | 99.4 | 1.808 | 90.8 | 1.393 | 69.9 | | |
| 12 | 1.972 | 99.0 | | | | | | |

$t_{90}$ (days) extrapolated according to Arrhenius equation:
$t_{90}$ at 4° C. = 3970 days
$t_{90}$ at 8° C. = 2000 days Similar stability data can be observed also for analogous solutions containing either doxorubicin hydrochloride at 5 mg/ml concentration, or 4'-epi-doxorubicin, 4'-desoxy-doxorubicin, 4'-desoxy-4'-iodo-doxorubicin, daunorubicin or 4-demethoxy-daunorubicin, as hydrochloride salts, at both 2 mg/ml and 5 mg/ml concentration.

EXAMPLE 3

| Composition | for 80 vials | (for 1 vial) |
|---|---|---|
| Doxorubicin · HCl | 8.0 g | (100 mg) |
| Hydrochloric acid 0.1N q.s. to | pH = 3 | (pH = 3) |
| Water for injections q.s. to | 0.4 l | (5 ml) |

Doxorubicin.HCl (8.0 g) was dissolved in 90 percent of the amount of water for injections, de-aerated by nitrogen bubbling. The hydrochloric acid was then added dropwise to adjust the pH of the solution to 3. Further de-aerated water for injections was then added to bring the solution to its final volume (0.4 l).

The solution was filtered through a 0.22 μm microporous membrane under nitrogen pressure. Volumes of 5 ml of the solution were distributed into type I-colourless glass vials having 5/7 ml capacity. The vials ere then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 12 weeks (4° C.).

The stability data obtained, using high performance liquid chromatogrpahy (HPLC) for the determination of potency, are reported in the following Table 3:

TABLE 3

INITIAL VALUES
Concentration: 20.06 mg/ml    pH = 2.95
Relative % Assay: 100.0

| | TEMPERATURE | | | | | | | |
|---|---|---|---|---|---|---|---|---|
| | 4° C. | | 35° C. | | 45° C. | | 55° C. | |
| TIME (weeks) | Conc. mg/ml | Rel. % Assay | Conc. mg/ml | Rel. % Assay | Conc. mg/ml | Rel. % Assay | Conc. mg/ml | Rel. % Assay |
| 1 | 20.06 | 100.0 | 19.56 | 97.5 | 17.84 | 88.9 | 12.31 | 61.4 |
| 2 | | | 18.87 | 94.1 | 15.61 | 77.8 | 7.09 | 35.3 |
| 3 | | | 18.24 | 90.9 | 13.41 | 66.8 | 3.13 | 15.6 |
| 4 | 19.91 | 99.2 | 17.51 | 87.3 | 11.07 | 55.2 | | |
| 12 | 19.80 | 98.7 | | | | | | |

$t_{90}$ (days) extrapolated according to Arrhenius equation:
$t_{90}$ at 4° C. = 3700 days
$t_{90}$ at 8° C. = 1780 days Similar stability data can be observed also for analogous solutions containing 4'-epi-doxorubicin or 4'-desoxydoxorubicin, as hydrochloride salts, at the same 20 mg/ml concentration.

EXAMPLE 4

| Composition | for 80 vials | (for 1 vial) |
|---|---|---|
| Doxorubicin · HCl | 0.80 | (10.0 mg) |
| Polyvinylpyrrolidone | 20.00 g | (250.0 mg) |
| Water for injections q.s. to | 0.40 l | (5.0 ml) |

Doxorubicin.HCl (0.80 g) was dissolved in 90 percent of the water for injections, de-aerated by nitrogen bubbling. The pH of the solution was not adjusted. Polyvinylpyrrolidone was added and dissolved under stirring and nitrogen bubbling. Further de-aerated water for injections was then added to bring the solution to its final volume (0.40 l).

The solution was filtered through a 0.22 μm microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 8 weeks (4° C.).

The stability data obtained, using high performance liquid chromatography (HPLC) for the determination of potency, are reported in the following Table 4:

TABLE 4

INITIAL VALUES
Concentration: 1.986 mg/ml    pH = 4.6
Relative % Assay: 100.0

| | TEMPERATURE | | | | | | | |
|---|---|---|---|---|---|---|---|---|
| | 4° C. | | 35° C. | | 45° C. | | 55° C. | |
| TIME (weeks) | Conc. mg/ml | Rel. % Assay | Conc. mg/ml | Rel. % Assay | Conc. mg/ml | Rel. % Assay | Conc. mg/ml | Rel. % Assay |
| 1 | 1.984 | 99.9 | 1.928 | 97.1 | 1.797 | 90.5 | 1.605 | 80.8 |
| 2 | | | 1.847 | 93.0 | 1.616 | 81.4 | 1.293 | 65.1 |
| 3 | | | 1.828 | 92.0 | 1.527 | 76.9 | 1.018 | 51.3 |
| 4 | 1.928 | 97.1 | 1.797 | 90.5 | 1.403 | 70.7 | | |
| 8 | 1.989 | 100.1 | | | | | | |

$t_{90}$ (days) extrapolated according to Arrhenius equation:
$t_{90}$ at 4° C. = 1460 days
$t_{90}$ at 8° C. = 835 days Similar stability data can be observed also for analogous solutions containing either doxorubicin hydrochloride at 5 mg/ml concentration, or 4'-epi-doxorubicin, 4'-desoxy-doxorubicin, 4'-desoxy-4'-iodo-doxorubicin, daunorubicin or 4-demethoxy-daunorubicin, as hydrochloride salts, at both 2 mg/ml and 5 mg/ml concentration.

EXAMPLE 5

| Composition | for 80 vials | (for 1 vial) |
| --- | --- | --- |
| Doxorubicin · HCl | 0.800 g | (10.00 mg) |
| N,N-Dimethylacetamide | 0.060 l | (0.75 ml) |
| Propylene glycol | 0.048 l | (0.60 ml) |
| Ethanol | 0.012 l | (0.15 ml) |
| Hydrochloric acid 0.1N q.s. to | pH = 3 | (pH = 3) |
| Water for injections q.s. to | 0.400 l | (5.00 ml) |

Doxorubicin.HCl (0.800 g) was dissolved in 90 percent of the amount of water for injections, de-aerated by nitrogen bubbling. N,N-Dimethylacetamide, propylene glycol and ethanol were subsequently added under stirring and nitrogen bubbling. The hydrochloric acid was then added dropwise to adjust the pH of the solution to 3. Further de-aerated water for injections was then added to bring the solution to its final volume (0.40 l).

The solution was filtered through a 0.22 μm microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 8 weeks (4° C.).

The stability data obtained, using high performance liquid chromatography (HPLC) for the determination of potency, are reported in the following Table 5:

Similar stability data can be observed also for analogous solutions containing either doxorubicin hydrochloride at 5 mg/ml concentration, or 4'-epi-doxorubicin, 4'-desoxy-doxorubicin, 4'-desoxy-4'-iodo-doxorubicin, daunorubicin or 4-demethoxy-daunorubicin, as hydrochloride salts, at both 2 mg/ml and 5 mg/ml concentration.

EXAMPLE 6

| Composition | for 80 vials | (for 1 vial) |
| --- | --- | --- |
| Doxorubicin · HCl | 0.8 g | (10.0 mg) |
| Polyvinylpyrrolidone | 20.0 g | (250.0 mg) |
| Hydrochloric acid 0.1N q.s. to | pH = 3 | (pH = 3) |
| Water for injections q.s. to | 0.4 l | (5.0 ml) |

Doxorubicin.HCl (0.8 g) was dissolved in 90 percent of the amount of water for injections, de-aerated by nitrogen bubbling. Polyvinylpyrrolidone was added and dissolved under stirring and nitrogen bubbling. The hydrochloric acid was then added dropwise to adjust the pH of the solution to 3. Further de-aerated water for injections was then added to bring the solution to its final volume (0.4 l).

The solution was filtered through a 0.22 μm microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 8 weeks (4° C.).

The stability data obtained, using high performance liquid chromatography (HPLC) for the determination of potency, are reported in the following Table 6:

TABLE 5

INITIAL VALUES
Concentration: 2.000 mg/ml    pH = 3.03
Relative % Assay: 100.0

| | TEMPERATURE | | | | | | | |
| --- | --- | --- | --- | --- | --- | --- | --- | --- |
| | 4° C. | | 35° C. | | 45° C. | | 55° C. | |
| TIME (weeks) | Conc. mg/ml | Rel. % Assay | Conc. mg/ml | Rel. % Assay | Conc. mg/ml | Rel. % Assay | Conc. mg/ml | Rel. % Assay |
| 1 | | | 1.892 | 94.6 | 1.735 | 86.7 | 1.495 | 74.7 |
| 2 | 1.993 | 99.7 | 1.927 | 96.4 | 1.624 | 81.2 | 1.212 | 60.6 |
| 3 | | | 1.908 | 95.4 | 1.432 | 71.6 | 1.032 | 51.6 |
| 4 | 2.00 | 100.0 | 1.863 | 93.2 | 1.266 | 63.3 | | |
| 8 | 1.960 | 98.0 | | | | | | |

$t_{90}$ (days) extrapolated according to Arrhenius equation:
$t_{90}$ at 4° C. = 4360 days
$t_{90}$ at 8° C. = 2200 days

TABLE 6

INITIAL VALUES
Concentration: 1.973 mg/ml   pH = 2.71
Relative % Assay: 100.0

| TIME (weeks) | TEMPERATURE | | | | | | | |
|---|---|---|---|---|---|---|---|---|
| | 4° C. | | 35° C. | | 45° C. | | 55° C. | |
| | Conc. mg/ml | Rel. % Assay | Conc. mg/ml | Rel. % Assay | Conc. mg/ml | Rel. % Assay | Conc. mg/ml | Rel. % Assay |
| 1 | 2.028 | 102.8 | 1.944 | 98.5 | 1.791 | 90.8 | 1.477 | 74.9 |
| 2 | | | 1.885 | 95.5 | 1.582 | 80.2 | 0.972 | 49.3 |
| 3 | | | 1.840 | 93.2 | 1.402 | 71.0 | 0.632 | 32.0 |
| 4 | 1.913 | 97.0 | 1.853 | 93.9 | 1.273 | 64.5 | | |
| 8 | 1.972 | 99.9 | | | | | | |

$t_{90}$ (days) extrapolated according to Arrhenius equation:
$t_{90}$ at 4° C. = 5560 days
$t_{90}$ at 8° C. = 2670 days Similar stability data can be observed also for analogous solutions containing either doxorubicin hydrochloride at 5 mg/ml concentration, or 4'-epi-doxorubicin, 4'-desoxy-doxorubicin, 4'-desoxy-4'-iodo-doxorubicin, daunorubicin or 4-demethoxy-daunorubicin, as hydrochloride salts, at both 2 mg/ml and 5 mg/ml concentration.

EXAMPLE 7

| Composition | for 80 vials | (for 1 vial) |
|---|---|---|
| Doxorubicin · HCl | 8.00 g | (100.0 mg) |
| N,N-Dimethylacetamide | 0.12 l | (1.5 ml) |
| Hydrochloric acid 0.1N q.s. to | pH = 3 | (pH = 3) |
| Water for injections q.s. to | 0.40 l | (5.0 ml) |

Doxorubicin.HCl (8.00 g) was dissolved in 90 percent of the amount of water for injections, de-aerated by nitrogen bubbling. N,N-Dimethylacetamide was added under stirring and nitrogen bubbling. The hydrochloric acid was then added dropwise to adjust the pH of the solution to 3. Further de-aerated water for injections was then added to bring the solution to its final volume (0.40 l).

The solution was filtered through a 0.22 μm microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 8 weeks (4° C.).

The stability data obtained, using high performance liquid chromatography (HPLC) for the determination of potency, are reported in the following Table 7:

TABLE 7

INITIAL VALUES
Concentration: 19.32 mg/ml   pH = 2.96
Relative % Assay: 100.0

| TIME (weeks) | TEMPERATURE | | | | | | | |
|---|---|---|---|---|---|---|---|---|
| | 4° C. | | 35° C. | | 45° C. | | 55° C. | |
| | Conc. mg/ml | Rel. % Assay | Conc. mg/ml | Rel. % Assay | Conc. mg/ml | Rel. % Assay | Conc. mg/ml | Rel. % Assay |
| 1 | 20.1 | 103.5 | 19.14 | 99.1 | 17.34 | 89.8 | 15.57 | 80.6 |
| 2 | | | 19.20 | 99.4 | 15.77 | 81.6 | 12.94 | 67.0 |
| 3 | | | 18.06 | 93.5 | 14.85 | 76.9 | 11.61 | 60.1 |
| 4 | 20.03 | 103.7 | 17.81 | 92.2 | 13.78 | 71.3 | | |
| 8 | 19.99 | 103.5 | | | | | | |

$t_{90}$ (days) extrapolated according to Arrhenius equation:
$t_{90}$ at 4° C. = 1310 days
$t_{90}$ at 8° C. = 770 days Similar stability data can be observed also for analogous solutions containing 4'-epi-doxorubicin, 4'-desoxy-doxorubicin, as hydrochloride salts, at the same 20 mg/ml concentration.

EXAMPLE 8

| Composition | for 80 vials | (for 1 vial) |
|---|---|---|
| Doxorubicin · HCl | 0.80 g | (10.0 mg) |
| Ethanol | 0.12 l | (1.5 ml) |
| Hydrochloric acid 0.1N q.s. to | pH = 3 | (pH = 3) |
| Water for injections q.s. to | 0.40 l | (5.0 ml) |

Doxorubicin.HCl (0.80 g) was dissolved in 90 percent of the amount of water for injections, de-aerated by nitrogen bubbling. Ethanol was added under stirring and nitrogen bubbling. Hydrochloric acid 0.1 N was then added dropwise to adjust the pH of the solution to 3. De-aerated water for injections was then added to bring the solution to its final volume (0.40 l).

The solution was filtered through a 0.22 μm microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 12 weeks (4° C.).

The stability data obtained, using high performance liquid chromatography (HPLC) for the determination of potency, are reported in the following Table 8:

doxorubicin, 4'-desoxy-4'-iodo-doxorubicin, daunorubicin or 4-demethoxy-daunorubicin, as hydrochloride salts, at both 2 mg/ml and 5 mg/ml concentration.

EXAMPLE 9

| Composition | for 80 vials | (for 1 vial) |
|---|---|---|
| Doxorubicin · HCl | 8.000 g | (100.00 mg) |
| N,N-Dimethylacetamide | 0.060 l | (0.75 ml) |
| Propylene glycol | 0.048 l | (0.60 ml) |
| Ethanol | 0.012 l | (0.15 ml) |
| Hydrochloric acid 0.1N q.s. to | pH = 3 | (pH = 3) |
| Water for injections q.s. to | 0.400 l | (5.00 ml) |

Duxorubicin.HCl (8.000 g) was dissolved in 90 percent of the amount of water for injections, de-aerated by nitrogen bubbling. N,N-Dimethylacetamide, propylene glycol and ethanol were subsequently added under stirring and nitrogen bubbling. The hydrochloric acid was then added dropwise to adjust the pH of the solution to 3. Further de-aerated water for injections was then added to bring the solution to its final volume (0.400 l).

The solution was filtered through a 0.22 μm microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials were tested. The vials were stored at temperatures of 55° C., 45° C. and 35° C. (accelerated stability controls) and at 4° C. for up to 3 weeks (55° C.), 4 weeks (45° C. and 35° C.) and 8 weeks (4° C.).

The stability data obtained, using high performance liquid chromatography (HPLC) for the determination of potency, are reported in the following Table 9:

TABLE 8

INITIAL VALUES
Concentration: 1.979 mg/ml    pH = 3.11
Relative % Assay: 100.0

| | TEMPERATURE | | | | | | | |
|---|---|---|---|---|---|---|---|---|
| | 4° C. | | 35° C. | | 45° C. | | 55° C. | |
| TIME (weeks) | Conc. mg/ml | Rel. % Assay | Conc. mg/ml | Rel. % Assay | Conc. mg/ml | Rel. % Assay | Conc. mg/ml | Rel. % Assay |
| 1 | 2.010 | 101.6 | 1.965 | 99.3 | 1.947 | 98.4 | 1.750 | 88.4 |
| 2 | | | 1.957 | 98.9 | 1.910 | 96.5 | 1.645 | 83.1 |
| 3 | | | 1.895 | 95.8 | 1.737 | 87.8 | 1.356 | 68.5 |
| 4 | 1.927 | 97.3 | 1.818 | 91.9 | 1.678 | 84.8 | | |
| 12 | 1.939 | 97.9 | | | | | | |

$t_{90}$ (days) extrapolated according to Arrhenius equation:
$t_{90}$ at 4° C. = 1270 days
$t_{90}$ at 8° C. = 780 days Similar stability data can be observed also for analogous solutions containing either doxorubicin hydrochloride at 5 mg/ml concentration, or 4'-epi-doxorubicin, 4'-desoxy-

TABLE 9

INITIAL VALUES
Concentration: 20.07 mg/ml    pH = 2.99
Relative % Assay: 100.0

| | TEMPERATURE | | | | | | | |
|---|---|---|---|---|---|---|---|---|
| | 4° C. | | 35° C. | | 45° C. | | 55° C. | |
| TIME (weeks) | Conc. mg/ml | Rel. % Assay | Conc. mg/ml | Rel. % Assay | Conc. mg/ml | Rel. % Assay | Conc. mg/ml | Rel. % Assay |
| 1 | | | 19.14 | 95.4 | 17.81 | 88.7 | 14.84 | 73.9 |
| 2 | 19.97 | 99.5 | 19.07 | 95.0 | 16.27 | 81.1 | 12.36 | 61.6 |
| 3 | | | 18.08 | 90.1 | 14.62 | 72.9 | 10.04 | 50.0 |
| 4 | 20.06 | 99.9 | 18.03 | 89.8 | 13.20 | 65.8 | | |
| 8 | 19.69 | 98.1 | | | | | | |

$t_{90}$ (days) extrapolated according to Arrhenius equation:
$t_{90}$ at 4° C. = 846 days
$t_{90}$ at 8° C. = 505 days Similar stability data can be observed for analogous solutions containing 4'-epi-doxorubicin or 4'-desoxy-doxorubicin, as hydrochloride salts, at the same 20 mg/ml concentration.

EXAMPLE 10

| Composition | for 80 vials | (for 1 vial) |
|---|---|---|
| Doxorubicin · HCl | 8.0 g | (100.0 mg) |
| Polyvinylpyrrolidone | 20.0 g | (250.0 mg) |
| Hydrochloric acid 0.1N q.s. to | pH = 3 | (pH = 3) |
| Water for injections q.s. to | 0.4 l | (5.0 ml) |

Doxorubicin.HCl (8.0 g) was dissolved in 90 percent of the amount of water for injections, de-aerated by nitrogen bubbling. Polyvinylpyrrolidone was added and dissolved under stirring and nitrogen bubbling. The hydrochloric acid was then added dropwise to adjust the pH of the solution to 3. Further de-aerated water for injections was then added to bring the solution to its final volume (0.4 l).

The solution was filtered through a 0.22 μm microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 8 weeks (4° C.).

The stability data obtained, using high performance liquid chromatography (HPLC) for the determination of potency, are reported in the following Table 10:

TABLE 10

INITIAL VALUES
Concentration: 19.57 mg/ml    pH = 2.62
Relative % Assay: 100.0

| | TEMPERATURE | | | | | | | |
|---|---|---|---|---|---|---|---|---|
| | 4° C. | | 35° C. | | 45° C. | | 55° C. | |
| TIME (weeks) | Conc. mg/ml | Rel. % Assay | Conc. mg/ml | Rel. % Assay | Conc. mg/ml | Rel. % Assay | Conc. mg/ml | Rel. % Assay |
| 1 | 19.54 | 99.9 | 19.11 | 97.6 | 16.88 | 86.2 | 12.48 | 63.8 |
| 2 | | | 18.43 | 94.2 | 14.13 | 72.2 | 6.00 | 30.7 |
| 3 | | | 18.02 | 92.1 | 11.57 | 59.1 | 2.61 | 13.3 |
| 4 | 19.58 | 100.1 | 17.36 | 88.7 | 9.23 | 47.2 | | |
| 8 | 19.34 | 98.8 | | | | | | |

$t_{90}$ (days) extrapolated according to Arrhenius equation:
$t_{90}$ at 4° C. = 2540 days
$t_{90}$ at 8° C. = 1290 days Similar stability data can be observed for analogous solutions containing 4'-epi-doxorubicin or 4'-desoxy-doxorubicin, as hydrochloride salts, at the same 20 mg/ml concentration.

EXAMPLE 11

| Composition | for 80 vials | (for 1 vial) |
|---|---|---|
| Doxorubicin · HCl | 0.80 g | (10.0 mg) |
| N,N-Dimethylacetamide | 0.12 l | (1.5 ml) |
| Hydrochloric acid 0.1N q.s. to | pH = 3 | (pH = 3) |
| Water for injections q.s. to | 0.40 l | (5.0 ml) |

Doxorubicin.HCl (0.80 g) was dissolved in 90 percent of the amount of water for injections, de-aerated by nitrogen bubbling. N,N-Dimethylacetamide was added under stirring and nitrogen bubbling. Hydrochloric acid 0.1 N was then added dropwise to adjust the pH of the solution to 3. De-aerated water for injections was finally added to bring the solution to its final volume (0.40 l).

The solution was filtered through a 0.22 μm microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 8 weeks (4° C.).

The stability data obtained, using high performance liquid chromatography (HPLC) for the determination of potency, are reported in the following Table 11:

Similar stability data can be observed also for analogous solutions containing either doxorubicin hydrochloride at 5 mg/ml concentration, or 4'-epi-doxorubicin, 4'-desoxy-doxorubicin, 4'-epi-desoxy-4'-iodo-doxorubicin, daunorubicin or 4-demethoxy-deunorubicin, as hydrochloride salts, at both 2 mg/ml and 5 mg/ml concentration.

EXAMPLE 12

| Composition | for 80 vials | (for 1 vial) |
|---|---|---|
| Doxorubicin · HCl | 0.80 g | (10.0 mg) |
| Propylene glycol | 0.12 l | (1.5 ml) |
| Hydrochloric acid 0.1N q.s. to | pH = 3 | (pH = 3) |
| Water for injections q.s. to | 0.40 l | (5.0 ml) |

Doxorubicin.HCl (0.80 g) was dissolved in 90 percent of the amount of water for injections de-aerated by nitrogen bubbling. Propylene glycol was added under stirring and nitrogen bubbling. Hydrochloric acid 0.1 N was then added dropwise to adjust the pH of the solution to 3. De-aerated water for injections was finally added to bring the solution to its final volume (0.40 l).

The solution was filtered through a 0.22 μm microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 4 weeks (4° C.).

The stability data obtained, using high performance liquid chromatography (HPLC) for the determination of potency, are reported in the following Table 12:

TABLE 11

INITIAL VALUES
Concentration: 1.826 mg/ml     pH = 3.14
Relative % Assay: 100.0

| | TEMPERATURE | | | | | | | |
|---|---|---|---|---|---|---|---|---|
| | 4° C. | | 35° C. | | 45° C. | | 55° C. | |
| TIME (weeks) | Conc. mg/ml | Rel. % Assay | Conc. mg/ml | Rel. % Assay | Conc. mg/ml | Rel. % Assay | Conc. mg/ml | Rel. % Assay |
| 1 | 1.830 | 100.2 | 1.812 | 99.2 | 1.784 | 97.7 | 1.605 | 87.9 |
| 2 | 1.818 | 99.6 | 1.781 | 97.5 | 1.554 | 85.1 | 1.292 | 70.8 |
| 3 | | | 1.743 | 95.4 | 1.409 | 77.2 | 1.018 | 55.7 |
| 4 | 1.823 | 99.8 | 1.734 | 95.0 | 1.369 | 75.0 | | |
| 8 | 1.792 | 98.2 | | | | | | |

$t_{90}$ (days) extrapolated according to Arrhenius equation:
$t_{90}$ at 4° C. = 5815 days
$t_{90}$ at 8° C. = 2920 days

TABLE 12

INITIAL VALUES
Concentration: 1.982 mg/ml   pH = 3.11
Relative % Assay: 100.0

| TIME (weeks) | TEMPERATURE | | | | | | | |
|---|---|---|---|---|---|---|---|---|
| | 4° C. | | 35° C. | | 45° C. | | 55° C. | |
| | Conc. mg/ml | Rel. % Assay | Conc. mg/ml | Rel. % Assay | Conc. mg/ml | Rel. % Assay | Conc. mg/ml | Rel. % Assay |
| 1 | 1.972 | 99.5 | 1.934 | 97.6 | 1.889 | 95.3 | 1.705 | 86.0 |
| 2 | | | 1.952 | 98.5 | 1.795 | 90.6 | 1.483 | 74.8 |
| 3 | | | 1.935 | 97.6 | 1.699 | 85.7 | 1.153 | 58.2 |
| 4 | 2.056 | 103.7 | 1.788 | 90.2 | 1.460 | 73.7 | | |

$t_{90}$ (days) extrapolated according to Arrhenius equation:
$t_{90}$ at 4° C. = 1794 days
$t_{90}$ at 8° C. = 1025 days Similar stability data can be observed also for analogous solutions containing either doxorubicin hydrochloride at 5 mg/ml concentration, or 4'-epi-doxorubicin, 4'-desoxy-doxorubicin, 4'-desoxy-4'-iodo-doxorubicin, daunorubicin or 4-demethoxy-daunorubicin, as hydrochloride salts, at both 2 mg/ml 5 mg/ml concentration.

EXAMPLE 13

| Composition | for 80 vials | (for 1 vial) |
|---|---|---|
| Doxorubicin · HCl | 0.80 g | (10.0 mg) |
| Polyethylene glycol 400 | 0.12 l | (1.5 ml) |
| Hydrochloric acid 0.1N q.s. to | pH = 3 | (pH = 3) |
| Water for injections q.s. to | 0.40 l | (5.0 ml) |

Doxorubicin.HCl (0.80 g) was dissolved in 90 percent of the amount of water for injections, de-aerated by nitrogen bubbling. Polyethylene glycol 400 was added under stirring and nitrogen bubbling. Hydrochloric acid 0.1 N was then added dropwise to adjust the pH of the solution to 3. De-aerated water for injections was finally added to bring the solution to its final volume (0.40 l).

The solution was filtered through a 0.22 μm microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 4 weeks (4° C.).

The stability data obtained, using high performance liquid chromatography (HPLC) for the determination of potency, are reported in the following Table 13:

TABLE 13

INITIAL VALUES
Concentration: 1.907 mg/ml   pH = 3.07
Relative % Assay: 100.0

| TIME (weeks) | TEMPERATURE | | | | | | | |
|---|---|---|---|---|---|---|---|---|
| | 4° C. | | 35° C. | | 45° C. | | 55° C. | |
| | Conc. mg/ml | Rel. % Assay | Conc. mg/ml | Rel. % Assay | Conc. mg/ml | Rel. % Assay | Conc. mg/ml | Rel. % Assay |
| 1 | 1.871 | 98.1 | 1.797 | 94.2 | 1.668 | 87.5 | 1.484 | 77.8 |
| 2 | | | 1.710 | 89.7 | 1.608 | 84.3 | 1.237 | 64.9 |
| 3 | | | 1.739 | 91.2 | 1.551 | 81.3 | 1.007 | 52.8 |
| 4 | 1.873 | 98.2 | 1.693 | 88.8 | 1.453 | 76.2 | | |

$t_{90}$ (days) extrapolated according to Arrhenius equation:
$t_{90}$ at 4° C. = 1130 days
$t_{90}$ at 8° C. = 680 days Similar stability data can be observed also for analogous solutions containing either doxorubicin hydrochloride at 5 mg/ml concentration, or 4'-epi-doxorubicin, 4'-desoxy-doxorubicin, 4'-desoxy-4'-iodo-doxorubicin, daunorubicin or 4-demethoxy-daunorubicin, as hydrochloride salts, at both 2 mg/ml and 5 mg/ml concentration.

EXAMPLE 14

| Composition | for 80 vials | (for 1 vial) |
|---|---|---|
| Doxorubicin · HCl | 0.8 g | (10 mg) |
| Hydrochloric acid 0.1N q.s. to | pH = 3 | (pH = 3) |
| Water for injections q.s. to | 0.4 l | (5 ml) |

Doxorubicin.HCl (0.8 g) was dissolved in 90 percent of the amount of water for injections, de-aerated by nitrogen bubbling. The hydrochloric acid was then added dropwise to adjust the pH of the solution to 3. Further de-aerated water for injections was then added to bring the solution to its final volume (0.4 l).

The solution was filtered through a 0.22 $\mu$m microporous membrane under nitrogen pressure. Volumes of 5 ml of the solution were distributed into type I-colourless glass vials having 5/7 ml capacity. The vials were then closed with chlorobutyl teflon-faced rubber stoppers and sealed with aluminium caps.

The stability of the solutions in the vials was tested. The vials were stored at temperatures of 4° C. and 8° C. for up to 6 months.

The stability data obtained, using high performance liquid chromatography (HPLC) for the determination of potency, are reported in the following Table 14:

TABLE 14

| INITIAL VALUES | | | | |
|---|---|---|---|---|
| Concentration: 2.039 mg/ml | | pH = 3.06 | | |
| Relative % Assay: 100.0 | | | | |
| | TEMPERATURE | | | |
| | 4° C. | | 8° C. | |
| TIME (weeks) | Conc. mg/ml | Rel. % Assay | Conc. mg/ml | Rel. % Assay |
| 1 | 1.983 | 97.3 | 1.959 | 96.1 |
| 3 | 1.984 | 97.3 | 1.983 | 97.3 |
| 6 | 2.012 | 98.7 | 2.002 | 98.2 |

At the same conditions, similar stability data can be generally observed also for the other solutions mentioned in the preceding examples.

We claim:

1. A sterile, pyrogen-free, anthracycline glycoside solution which consists essentially of a physiologically acceptable salt of an anthracycline glycoside dissolved in a physiologically acceptable solvent therefor, which has not been reconstituted from a lyophilizate and which has a pH of from 2.5 to 6.5.

2. A solution according to claim 1 in a sealed container.

3. A solution according to claim 1 or 2, wherein the anthracycline glycoside is selected from the group consisting of doxorubicin, 4'-epi-doxorubicin, 4'-desoxy-doxorubicin, 4'-desoxy-4'-iodo-doxorubicin, daunorubicin and 4-demethoxy-daunorubicin.

4. A solution according to claim 3, wherein the anthracycline glycoside is doxorubicin.

5. A solution according to claim 1, wherein the physiologically acceptable salt of the anthracycline glycoside is the salt with a physiologically acceptable acid selected from the group consisting of hydrochloric, hydrobromic, sulfuric, phosphoric, nitric, acetic, succinic, tartaric, ascorbic, citric, glutamic, benzoic, methanesulfonic and ethanesulfonic acid.

6. A solution according to claim 5, wherein the physiologically acceptable salt of the anthracycline glycoside is the salt with hydrochloric acid.

7. A solution according to claim 1, having a pH of from 2.5 to 5.5.

8. A solution according to claim 7, having pH 3 or pH 5.

9. A solution according to claim 1, wherein the physiologically acceptable solvent for the anthracycline glycoside is selected from the group consisting of water, ethanol, polyethyleneglycol, dimethylacetamide and mixtures thereof.

10. A solution according to claim 9, wherein the physiologically acceptable solvent is water.

11. A solution according to claim 1, wherein the concentration of the anthracycline glycoside is from 0.1 mg/ml to 100 mg/ml.

12. A solution according to claim 11, wherein the concentration of the anthracycline glycoside is from 0.1 mg/ml to 50 mg/ml.

13. A solution according to claim 12, wherein the concentration of the anthracycline glycoside is from 1 mg/ml to 20 mg/ml.

14. A sterile, pyrogen-free, doxorubicin solution which consists essentially of a physiologically acceptable salt of doxorubicin dissolved in a physiologically acceptable solvent therefor, which has not been reconstituted from a lyophilizate and which has a pH of from 2.5 to 6.5.

15. A solution according to claim 14 in a sealed container.

16. A solution according to claim 14, wherein the physiologically acceptable salt of doxorubicin is the salt with a physiologically acceptable acid selected from the group consisting of hydrochloric, hydrobromic, sulfuric, phosphoric, nitric, acetic, succinic, tartaric, ascorbic, citric, glutamic, benzoic, methanesulfonic and ethanesulfonic acid.

17. A solution according to claim 16, wherein the physiologically acceptable salt of doxorubicin is the salt with hydrochloric acid.

18. A solution according to claim 14, having a pH of from 2.5 to 5.5.

19. A solution according to claim 18, having pH 3 or pH 5.

20. A solution according to claim 14, wherein the physiologically acceptable solvent for doxorubicin is selected from the group consisting of water, ethanol, polyethyleneglycol, dimethylacetamide and mixtures thereof.

21. A solution according to claim 20, wherein the physiologically acceptable solvent is water.

22. A solution according to claim 14, wherein the concentration for doxorubicin is from 0.1 mg/ml to 100 mg/ml.

23. A solution according to claim 22, wherein the concentration of doxorubicin is from 2 mg/ml to 50 mg/ml.

24. A solution according to claim 23, wherein the concentration of doxorubicin is 2 mg/ml to 20 mg/ml.

25. A solution according to claim 24, wherein the concentration of doxorubicin is 2 mg/ml or 5 mg/ml.

26. A process for producing the solution of claim 1, which process comprises dissolving a physiologically acceptable salt of the anthracycline glycoside, which salt is not in the form of a lyophilizate, in a physiologically acceptable solvent therefor; optionally adding a physiologically acceptable acid or buffer to adjust the pH within the said range as desired; and passing the resulting solution through a sterilising filter.

27. A process according to claim 26, wherein an additional component selected from the group consisting of co-solubilizing agents, tonicity adjustment agents and preservatives is added to the solution prior to passing the solution through a sterilizing filter.

28. A process according to claim 27, wherein the co-solubilizing agent is polyvinylpyrrolidone.

29. A method of inhibiting the growth of a tumour selected from the group consisting of sarcomas, carcinomas, lymphomas, neuroblastoma, melanoma, myeloma, leukemias and Wilms tumour, which method comprises administering to a host suffering from said tumour the solution of claim 1, containing the active drug substance in an amount sufficient to inhibit the growth of said tumour.

30. A method according to claim 29, wherein the tumour is selected from the group consisting of Moloney Sarcoma Virus, Sarcoma 180 Ascites, Solid Sarcoma 180, gross transplantable leukemia, L 1210 leukemia and lymphocitic P 388 leukemia.

* * * * *